(12) United States Patent
Jordan et al.

(10) Patent No.: US 8,354,415 B2
(45) Date of Patent: Jan. 15, 2013

(54) THIENOPYRIMIDINE COMPOUNDS AND COMPOSITIONS

(75) Inventors: Allan Jordan, Winnersh (GB); Simon Bedford, Winnersh (GB); Klenke Burkhard, Winnersh (GB); Ian Yule, Winnersh (GB); Karine Poullennec, Winnersh (GB)

(73) Assignee: Vernalis (R&D) Ltd. (GB)

( * ) Notice: Subject to any disclaimer, the term of this patent is extended or adjusted under 35 U.S.C. 154(b) by 261 days.

(21) Appl. No.: 12/678,376

(22) PCT Filed: Sep. 19, 2008

(86) PCT No.: PCT/GB2008/003180
§ 371 (c)(1),
(2), (4) Date: Aug. 10, 2010

(87) PCT Pub. No.: WO2009/037468
PCT Pub. Date: Mar. 26, 2009

(65) Prior Publication Data
US 2010/0298349 A1   Nov. 25, 2010

(30) Foreign Application Priority Data
Sep. 21, 2007 (GB) .................................. 0718432.8

(51) Int. Cl.
C07D 495/04 (2006.01)
A61K 31/519 (2006.01)
A61P 11/06 (2006.01)
A61P 11/08 (2006.01)
A61P 29/00 (2006.01)

(52) U.S. Cl. ..................................... 514/260.1; 544/278

(58) Field of Classification Search .................. 544/278; 514/260.1
See application file for complete search history.

(56) References Cited

FOREIGN PATENT DOCUMENTS
WO         0102409 A         1/2001

OTHER PUBLICATIONS
International Search Report dated Oct. Jul. 11, 2008.

*Primary Examiner* — Susanna Moore
(74) *Attorney, Agent, or Firm* — Banner & Witcoff, Ltd.

(57) ABSTRACT

Compounds of formula (I) are $A_{2B}$ wherein R1 and R2 are independently selected from hydrogen, or optionally substituted $C_1$-$C_6$ alkyl, $C_1$-$C_6$ alkoxy-($C_1$-$C_6$)-alkyl, $C_3$-$C_8$ cycloalkyl, aryl, heteroaryl, aryl-($C_1$-$C_6$)-alkyl, or heteroaryl-($C_1$-$C_6$)-alkyl; or $R_{-1}$ and $R_2$ taken together with the nitrogen atom to which they are attached form an optionally substituted 5- or 6-membered ring; $R_3$ and $R_4$ are independently selected from hydrogen, or optionally substituted $C_1$-$C_6$ alkyl, $C_1$-$C_6$ alkoxy-($C_1$-$C_6$)-alkyl, $C_3$-$C_8$ cycloalkyl, aryl, heteroaryl, aryl-($C_1$-$C_6$)-alkyl, or heteroaryl-$C_1$-$C_6$)-alkyl; or $R_3$ and $R_4$ taken together with the nitrogen atom to which they are attached form an optionally substituted 5- or 6-membered ring; $R_5$ and $R_6$ are independently selected from hydrogen, $C_1$-$C_6$ alkyl, aryl, aryl-($C_1$-$C_6$)-alkyl, —$NHR_7$—N(—$R_8$)—$R_9$, —NH—(C=O)—$R_{10}$, —(C=O)—NH—$R_{11}$, —(C=O)—O—$R_{12}$, or halo; and $R_7$, $R_8$, $R_9$, $R_{10}$, $R_{11}$, and $R_{12}$ are independently selected from $C_1$-$C_6$ alkyl, aryl, aryl-($C_1$-$C_6$)-alkyl and heteroaryl.

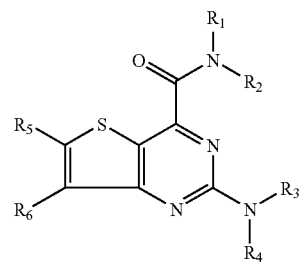

(I)

26 Claims, No Drawings

THIENOPYRIMIDINE COMPOUNDS AND COMPOSITIONS

CROSS REFERENCE TO RELATED APPLICATIONS

This application is a National Stage application of co-pending PCT application PCT/GB2008/003180 filed Sep. 19, 2008, which claims the benefit of Great Britain application number 0718432.8 filed Sep. 21, 2007. These applications are incorporated herein by reference in their entireties.

This invention relates to novel thienopyrimidine derivatives having $A_{2B}$ receptor antagonistic activity, to the use of such compounds in medicine, in relation to the treatment of disorders which are responsive to antagonism of the $A_{2B}$ receptor such as nociception, asthma, COPD, inflammatory disorders, diabetes, diabetic retinopathy and cancer, and to pharmaceutical compositions containing such compounds.

BACKGROUND TO THE INVENTION

Adenosine is a naturally occurring purine nucleoside, the effects of which include stimulation of nociception afferents, bronchconstriction, immunosupression, vasodilation, inhibition of platelet aggregation, cardiac depression and inhibition of neurotransmitter release.

Adenosine produces a wide range of pharmacological effects mediated by activation of specific cell surface receptors, which are members of the G-protein coupled receptor family. Four subtypes of adenosine receptors have been identified, designated $A_1$, $A_{2A}$, $A_{2B}$ and $A_3$.

The $A_{2B}$ adenosine receptor subtype is coupled to the $G_s$ G-protein and stimulates adenylyl cyclase activity. Although significant advancement has been made in the understanding of the molecular pharmacology and physiology of $A_{2B}$ adenosine receptors, due to the lack of highly potent and selective ligands for this receptor subtype, many questions about the patho-physiological role of $A_{2B}$ receptors are yet to be resolved (Feoktistov and Biaggioni, Pharmacological Reviews (1997), 49(4), 381-402).

$A_{2B}$ receptors have been implicated in:
(i) the regulation of mast cell secretion (Feoktistov and Biaggioni., Journal of Clinical Investigation (1995), 96(4), 1979-86).
(ii) pain (Abo-Salem et al., Journal of Pharmacology and Experimental Therapeutics (2004), 308(1), 358-366.).
(iii) inflammation (Yang et al., Journal of Clinical Investigation (2006), 116(7), 1913-1923).
(iv) cancer (Zeng et al., Drug Development Research (2003), 58(4), 405-411).
(v) diabetes (Harada et al., Journal of Medicinal Chemistry (2001), 44(2), 170-179).
(vi) gene expression (Boyle et al., Arthritis & Rheumatism (1996), 39(6), 923-930).
(vii) cell growth (Dubey et al., Hypertension (1996), 27(3 Pt 2), 786-93 Hypertension (1996), 27(3 Pt 2), 786-93, Dubey et al., Hypertension (1998), 31(1 Pt 2), 516-21).
(viii) intestinal functions (Murthy et al., Journal of Neurochemistry (1995), 64(1), 77-84).
(ix) neurosecretion (Mateo et al., 1995).
(x) vascular tone (Haynes et al., American Journal of Physiology (1995), 268(5, Pt. 2), H1862-H1868).
(xi) asthma (Feoktistov et al., Trends in pharmacological sciences (1998), 19(4), 148-153; Holgate, British Journal of Pharmacology (2005), 145(8), 1009-1015).
(xii) COPD (Van den Berge et al., Drugs in R&D (2007), 8(1), 13-23).

Thus, there remains a medical need for low molecular weight $A_{2B}$ antagonists with pharmacokinetic and pharmacodynamic properties making them suitable for use as pharmaceutical agents. There also remains a medical need for new treatments of disorders mediated by the $A_{2B}$ receptor, particularly nociception, asthma, COPD, inflammatory disorders, diabetes, diabetic retinopathy and cancer. The object of the present invention is to provide such pharmaceutical agents and treatments.

It has now been found that certain thienopyrimidine derivatives show efficacy as $A_{2B}$ antagonists.

BRIEF DESCRIPTION OF THE INVENTION

The present invention relates to a class of substituted thienopyrimidine compounds useful as $A_{2B}$ antagonists, for example, for the treatment of nociception, asthma, COPD, inflammatory disorders, diabetes, diabetic retinopathy and cancer. A core thieno-pyrimidine bicyclic ring, with substitution on the pyrimidine portion by an amido group in addition to an amino group are principle characterising features of the compounds with which the invention is concerned.

DETAILED DESCRIPTION OF THE INVENTION

According to the present invention, there is provided a compound of formula (I) or a pharmaceutically acceptable salt, hydrate or solvate thereof:

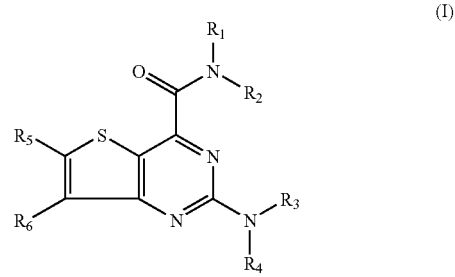

(I)

wherein
$R_1$ and $R_2$ are independently selected from hydrogen, or optionally substituted $C_1$-$C_6$ alkyl, $C_1$-$C_6$ alkoxy-($C_1$-$C_6$)-alkyl, $C_3$-$C_8$ cycloalkyl, aryl, heteroaryl, aryl-($C_1$-$C_6$)-alkyl, or heteroaryl-($C_1$-$C_6$)-alkyl;
or $R_1$ and $R_2$ taken together with the nitrogen atom to which they are attached form an optionally substituted 5- or 6-membered ring;
$R_3$ and $R_4$ are independently selected from hydrogen, or optionally substituted $C_1$-$C_6$ alkyl, $C_1$-$C_6$ alkoxy-($C_1$-$C_6$)-alkyl, $C_3$-$C_8$ cycloalkyl, aryl, heteroaryl, aryl-($C_1$-$C_6$)-alkyl, or heteroaryl-($C_1$-$C_6$)-alkyl;
or $R_3$ and $R_4$ taken together with the nitrogen atom to which they are attached form an optionally substituted 5- or 6-membered ring;
$R_5$ and $R_6$ are independently selected from hydrogen, $C_1$-$C_6$ alkyl, aryl, aryl-($C_1$-$C_6$)-alkyl, —$NHR_7$, —$N(-R_8)$—$R_9$, —NH—(C=O)—$R_{10}$, —(C=O)—NH—$R_{11}$, —(C=O)—O—$R_{12}$, or halo; and
$R_7$, $R_8$, $R_9$, $R_{10}$, $R_{11}$, and $R_{12}$ are independently selected from $C_1$-$C_6$ alkyl, aryl, aryl-($C_1$-$C_6$)-alkyl and heteroaryl.

The active compounds of formula (I) are antagonists of the $A_{2B}$ receptor and are useful for the treatment, prevention and suppression of disorders mediated by the $A_{2B}$ receptor. Such disorders include nociception; asthma; chronic obstructive pulmonary disease (COPD); inflammatory diseases such as rheumatoid arthritis, multiple sclerosis, lupus, psoriasis and inflammatory bowel disease; diabetes mellitus or diabetes insipidus; diabetic retinopathy and cancer.

According to a further embodiment of the present invention there is provided the use of a compound of formula (I), or a pharmaceutically acceptable salt, hydrate, solvate, or prodrug thereof, in the manufacture of a medicament for the treatment of disorders mediated by the adenosine $A_{2B}$ receptor.

According to a further embodiment of the present invention there is provided a method of treatment of a disorder mediated by the $A_{2B}$ receptor comprising administration to a subject in need of such treatment an effective dose of the compound of formula (I), or a pharmaceutically acceptable salt, hydrate, solvate, or prodrug thereof.

According to a further embodiment of the present invention there is provided a pharmaceutical composition comprising a compound of formula (I), or a pharmaceutically acceptable salt, hydrate, solvate, or prodrug thereof, and a pharmaceutically acceptable carrier.

As used herein, the term "$(C_a-C_b)$alkyl" wherein a and b are integers refers to a straight or branched chain alkyl radical having from a to b carbon atoms. Thus when a is 1 and b is 6, for example, the term includes methyl, ethyl, n-propyl, isopropyl, n-butyl, isobutyl, sec-butyl, t-butyl, n-pentyl and n-hexyl.

As used herein the term "divalent $(C_a-C_b)$alkylene radical" wherein a and b are integers refers to a saturated hydrocarbon chain having from a to b carbon atoms and two unsatisfied valences.

As used herein the term "$(C_a-C_b)$alkenyl" wherein a and b are integers refers to a straight or branched chain alkenyl moiety having from a to b carbon atoms having at least one double bond of either E or Z stereochemistry where applicable. The term includes, for example, vinyl, allyl, 1- and 2-butenyl and 2-methyl-2-propenyl.

As used herein the term "divalent $(C_a-C_b)$alkenylene radical" refers to a hydrocarbon chain having from a to b carbon atoms, at least one double bond, and two unsatisfied valences.

As used herein the term "cycloalkyl" refers to a saturated carbocyclic radical having from 3-8 carbon atoms and includes, for example, cyclopropyl, cyclobutyl, cyclopentyl, cyclohexyl, cycloheptyl and cyclooctyl.

As used herein the term "cycloalkenyl" refers to a carbocyclic radical having from 3-8 carbon atoms containing at least one double bond, and includes, for example, cyclopentenyl, cyclohexenyl, cycloheptenyl and cyclooctenyl.

As used herein the term "carbocyclic" refers to a mono- or bi-cyclic radical whose ring atoms are all carbon, and includes monocyclic aryl, cycloalkyl, and cycloalkenyl radicals, provided that no single ring present has more than 8 ring members. A "carbocyclic" group includes a mono-bridged or multiply-bridged cyclic alkyl group.

As used herein the term "aryl" refers to a mono-, bi- or tri-cyclic carbocyclic aromatic radical. Illustrative of such radicals are phenyl, biphenyl and napthyl.

As used herein the term "heteroaryl" refers to a mono-, bi- or tri-cyclic aromatic radical containing one or more heteroatoms selected from S, N and O. Illustrative of such radicals are thienyl, benzthienyl, furyl, benzfuryl, pyrrolyl, imidazolyl, benzimidazolyl, thiazolyl, benzthiazolyl, isothiazolyl, benzisothiazolyl, pyrazolyl, oxazolyl, benzoxazolyl, isoxazolyl, benzisoxazolyl, isothiazolyl, triazolyl, benztriazolyl, thiadiazolyl, oxadiazolyl, pyridinyl, pyridazinyl, pyrimidinyl, pyrazinyl, triazinyl, indolyl and indazolyl.

As used herein the unqualified term "heterocyclyl" or "heterocyclic" includes, "heteroaryl" as defined above, and in particular refers to a mono-, bi- or tri-cyclic non-aromatic radical containing one or more heteroatoms selected from S, N and O, to groups consisting of a monocyclic non-aromatic radical containing one or more such heteroatoms which is covalently linked to another such radical or to a monocyclic carbocyclic radical, and to a mono-, bi- or tri-cyclic non-aromatic radical containing one or more heteroatoms selected from S, N and O which is mono-bridged or multiply-bridged. Illustrative of such radicals are pyrrolyl, furanyl, thienyl, piperidinyl, imidazolyl, oxazolyl, isoxazolyl, thiazolyl, thiadiazolyl, pyrazolyl, pyridinyl, pyrrolidinyl, pyrimidinyl, morpholinyl, piperazinyl, indolyl, morpholinyl, benzfuranyl, pyranyl, isoxazolyl, benzimidazolyl, methylenedioxyphenyl, ethylenedioxyphenyl, maleimido and succinimido groups.

Unless otherwise specified in the context in which it occurs, the term "substituted" as applied to any moiety herein means substituted with at least one substituent, for example selected from $(C_1-C_6)$alkyl, $(C_1-C_6)$alkoxy, hydroxy, hydroxy$(C_1-C_6)$alkyl, mercapto, mercapto$(C_1-C_6)$alkyl, $(C_1-C_6)$alkylthio, halo (including fluoro and chloro), trifluoromethyl, trifluoromethoxy, nitro, nitrile (—CN), oxo, phenyl, —COOH, —COOR$^A$, —COR$^A$, —SO$_2$R$^A$, —CONH$_2$, —SO$_2$NH$_2$, —CONHR$^A$, —SO$_2$NHR$^A$, —CONR$^A$R$^B$, —SO$_2$NR$^A$R$^B$, —NH$_2$, —NHR$^A$, —NR$^A$R$^B$, —OCONH$_2$, —OCONHR$^A$, —OCONR$^A$R$^B$, —NHCOR$^A$, —NHCOOR$^A$, —NR$^B$COOR$^A$, —NHSO$_2$OR$^A$, —NR$^B$SO$_2$OR$^A$, —NHCONH$_2$, —NR$^A$CONH$_2$, —NHCONHR$^B$, —NR$^A$CONHR$^B$, —NHCONR$^A$R$^B$, or —NR$^A$CONR$^A$R$^B$ wherein R$^A$ and R$^B$ are independently a $(C_1-C_6)$alkyl group, or R$^A$ and R$^B$ when attached to the same nitrogen may form a cyclic amino ring such as a morpholinyl, piperidinyl or piperazinyl ring. An "optional substituent" or "substituent" may be one of the foregoing substituent groups.

As used herein the term "salt" includes base addition, acid addition and quaternary salts. Compounds of the invention which are acidic can form salts, including pharmaceutically or veterinarily acceptable salts, with bases such as alkali metal hydroxides, e.g. sodium and potassium hydroxides; alkaline earth metal hydroxides e.g. calcium, barium and magnesium hydroxides; with organic bases e.g. N-ethyl piperidine, dibenzylamine and the like. Those compounds (I) which are basic can form salts, including pharmaceutically or veterinarily acceptable salts with inorganic acids, e.g. with hydrohalic acids such as hydrochloric or hydrobromic acids, sulphuric acid, nitric acid or phosphoric acid and the like, and with organic acids e.g. with acetic, tartaric, succinic, fumaric, maleic, malic, salicylic, citric, methanesulphonic and p-toluene sulphonic acids and the like.

For a review on suitable salts, see Handbook of Pharmaceutical Salts: Properties, Selection, and Use by Stahl and Wermuth (Wiley-VCH, Weinheim, Germany, 2002).

The term 'solvate' is used herein to describe a molecular complex comprising the compound of the invention and a stoichiometric amount of one or more pharmaceutically acceptable solvent molecules, for example, ethanol. The term 'hydrate' is employed when said solvent is water.

Compounds with which the invention is concerned which may exist in one or more stereoisomeric form, because of the presence of asymmetric atoms or rotational restrictions, can exist as a number of stereoisomers with R or S stereochemistry at each chiral centre or as atropisomeres with R or S stereochemistry at each chiral axis. The invention includes all such enantiomers and diastereoisomers and mixtures thereof.

So-called 'pro-drugs' of the compounds of formula (I) are also within the scope of the invention. Thus certain derivatives of compounds of formula (I) which may have little or no pharmacological activity themselves can, when administered into or onto the body, be converted into compounds of formula (I) having the desired activity, for example, by hydrolytic cleavage. Such derivatives are referred to as 'prodrugs'. Further information on the use of prodrugs may be found in Pro-drugs as Novel Delivery Systems, Vol. 14, ACS Symposium Series (T. Higuchi and W. Stella) and Bioreversible Carriers in Drug Design, Pergamon Press, 1987 (ed. E. B. Roche, American Pharmaceutical Association).

Prodrugs in accordance with the invention can, for example, be produced by replacing appropriate functionalities present in the compounds of formula (I) with certain moieties known to those skilled in the art as 'pro-moieties' as described, for example, in Design of Prodrugs by H. Bundgaard (Elsevier, 1985).

Also included within the scope of the invention are metabolites of compounds of formula (I), that is, compounds formed in vivo upon administration of the drug. Some examples of metabolites include (i) where the compound of formula (I) contains a methyl group, an hydroxymethyl derivative thereof (—$CH_3$→—$CH_2OH$):
(ii) where the compound of formula (I) contains an alkoxy group, an hydroxy derivative thereof (—OR→—OH);
(iii) where the compound of formula (I) contains a tertiary amino group, a secondary amino derivative thereof (—$NR^1R^2$→—$NHR^1$ or —$NHR^2$);
(iv) where the compound of formula (I) contains a secondary amino group, a primary derivative thereof (—$NHR^1$→—$NH_2$);
(v) where the compound of formula (I) contains a phenyl moiety, a phenol derivative thereof (-Ph→-PhOH); and
(vi) where the compound of formula (I) contains an amide group, a carboxylic acid derivative thereof (—$CONH_2$→COOH).

The Group —$N(R_1)$—$R_2$

In the compounds in accordance with the invention, $R_1$ and $R_2$ are independently selected from hydrogen, or optionally substituted $C_1$-$C_6$ alkyl, $C_1$-$C_6$ alkoxy-($C_1$-$C_6$)-alkyl, $C_3$-$C_8$ cycloalkyl, aryl, heteroaryl, aryl-($C_1$-$C_6$)-alkyl, or heteroaryl-($C_1$-$C_6$)-alkyl.

In a subclass of compounds with which the invention is concerned, $R_1$ and $R_2$ are independently selected from hydrogen, $C_1$-$C_6$ alkyl, $C_1$-$C_6$ alkoxy-($C_1$-$C_6$)-alkyl, $C_3$-$C_8$ cycloalkyl, aryl-($C_1$-$C_6$)-alkyl, or heteroaryl-($C_1$-$C_6$)-alkyl.

In a further subclass of compounds with which the invention is concerned, $R_1$ is hydrogen and $R_2$ is selected from hydrogen, $C_1$-$C_6$ alkyl, $C_1$-$C_6$ alkoxy-($C_1$-$C_6$)-alkyl, $C_3$-$C_8$ cycloalkyl, aryl-($C_1$-$C_6$)-alkyl, or heteroaryl-($C_1$-$C_6$)-alkyl. In such cases, $R_2$ may be hydrogen, methyl, ethyl, isopropyl, 2-methoxy-ethyl, cyclopropyl, cyclopentyl, cyclohexyl, benzyl, 2-phenyl-ethyl, or pyrid-3-yl-methyl.

It is presently preferred that $R_1$ is hydrogen and $R_2$ is selected from $C_1$-$C_6$ alkyl, or $C_3$-$C_8$ cycloalkyl.

Particularly preferred are those compounds wherein $R_1$ is hydrogen and $R_2$ is methyl, ethyl, isopropyl, or cyclopropyl.

In another subclass of compounds with which the invention is concerned, $R_1$ and $R_2$ taken together with the nitrogen atom to which they are attached form an optionally substituted 5- or 6-membered ring.

Preferred compounds are those wherein $R_1$ and $R_2$ taken together with the nitrogen atom to which they are attached form an optionally substituted pyrrolidine or piperidine ring.

Particularly preferred are those compounds wherein $R_1$ and $R_2$ taken together with the nitrogen atom to which they are attached form pyrrolidin-1-yl or piperidin-1-yl.

The Group —$N(R_3)$—$R_4$

In the compounds in accordance with the invention, $R_3$ and $R_4$ are independently selected from hydrogen, or optionally substituted $C_1$-$C_6$ alkyl, $C_1$-$C_6$ alkoxy-($C_1$-$C_6$)-alkyl, $C_3$-$C_8$ cycloalkyl, aryl, heteroaryl, aryl-($C_1$-$C_6$)-alkyl, or heteroaryl-($C_1$-$C_6$)-alkyl.

In a subclass of compounds with which the invention is concerned, $R_3$ and $R_4$ are independently selected from hydrogen or heteroaryl-($C_1$-$C_6$)-alkyl.

In a further subclass of compounds with which the invention is concerned, $R_3$ is hydrogen and $R_4$ is heteroaryl-($C_1$-$C_6$)-alkyl. In such cases, $R_4$ includes methyl- or ethyl-substituted by an optionally substituted 5- or 6-membered heteroaryl ring.

Preferred compounds include those wherein $R_3$ is hydrogen and $R_4$ is $C_1$-$C_6$ alkyl substituted by pyridyl.

Particularly preferred at present are those compounds wherein $R_3$ is hydrogen and $R_4$ is pyrid-3-ylmethyl or 1-(pyrid-3-yl)ethyl.

In another subclass of compounds with which the invention is concerned, $R_3$ and $R_4$ taken together with the nitrogen atom to which they are attached form an optionally substituted 5- or 6-membered ring.

The Groups $R_5$ and $R_6$

In the compounds in accordance with the invention, $R_5$ and $R_6$ are independently selected from hydrogen, $C_1$-$C_6$ alkyl, aryl, aryl-($C_1$-$C_6$)-alkyl, —$NHR_7$, —$N$(—$R_8$)—$R_9$, —NH—(C=C)—$R_{10}$, —(C=C)—NH—$R_{11}$, —(C=C)—O—$R_{12}$, or halo; wherein $R_7$, $R_8$, $R_9$, $R_{10}$, $R_{11}$, and $R_{12}$ are independently selected from $C_1$-$C_6$ alkyl, aryl, aryl-($C_1$-$C_6$)-alkyl and heteroaryl.

It is presently preferred that both $R_5$ and $R_6$ are hydrogen.

Specific compounds with which the invention is concerned include those of the Examples.

The present invention may be employed in respect of a human or animal subject, more preferably a mammal, more preferably a human subject.

As used herein, the term "treatment" as used herein includes prophylactic treatment.

The compound of formula (I) may be used in combination with one or more additional drugs useful in the treatment of the disorders mentioned above, the components being in the same formulation or in separate formulations for administration simultaneously or sequentially.

It will be understood that the specific dose level for any particular patient will depend upon a variety of factors including the activity of the specific compound employed, the age, body weight, general health, sex, diet, time of administration, route of administration, rate of excretion, drug combination and the causative mechanism and severity of the particular disease undergoing therapy. In general, a suitable dose for orally administrable formulations will usually be in the range of 0.1 to 3000 mg, once, twice or three times per day, or the equivalent daily amount administered by infusion or other routes. However, optimum dose levels and frequency of dosing will be determined by clinical trials as is conventional in the art.

The compounds with which the invention is concerned may be prepared for administration by any route consistent with their pharmacokinetic properties. The orally administrable compositions may be in the form of tablets, capsules, powders, granules, lozenges, liquid or gel preparations, such as oral, topical, or sterile parenteral solutions or suspensions. Tablets and capsules for oral administration may be in unit dose presentation form, and may contain conventional excipients such as binding agents, for example syrup, acacia, gelatin, sorbitol, tragacanth, or polyvinyl-pyrrolidone; fillers for example lactose, sugar, maize-starch, calcium phosphate, sorbitol or glycine; tabletting lubricant, for example magnesium stearate, talc, polyethylene glycol or silica; disintegrants for example potato starch, or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives such as suspending agents, for example sorbitol, syrup, methyl cellulose, glucose syrup, gelatin hydrogenated edible fats; emulsifying agents, for example lecithin, sorbitan monooleate, or acacia; non-aqueous vehicles (which may include edible oils), for example almond oil, fractionated coconut oil, oily esters such as glycerine, propylene glycol, or ethyl alcohol; preservatives, for example methyl or propyl p-hydroxybenzoate or sorbic acid, and if desired conventional flavouring or colouring agents.

For topical application to the skin, the drug may be made up into a cream, lotion or ointment. Cream or ointment formulations which may be used for the drug are conventional formulations well known in the art, for example as described in standard textbooks of pharmaceutics such as the British Pharmacopoeia.

The active ingredient may also be administered parenterally in a sterile medium. Depending on the vehicle and concentration used, the drug can either be suspended or dissolved in the vehicle. Advantageously, adjuvants such as a local anaesthetic, preservative and buffering agents can be dissolved in the vehicle.

There are multiple synthetic strategies for the synthesis of the compounds (I) with which the present invention is concerned, but all rely on known chemistry, known to the synthetic organic chemist. Thus, compounds according to formula (I) can be synthesised according to procedures described in the standard literature and are well-known to the one skilled in the art. Typical literature sources are "Advanced organic chemistry", 4$^{th}$ Edition (Wiley), J March, "Comprehensive Organic Transformation", 2$^{nd}$ Edition (Wiley), R. C. Larock, "Handbook of Heterocyclic Chemistry", 2$^{nd}$ Edition (Pergamon), A. R. Katritzky), review articles such as found in "Synthesis", "Acc. Chem. Res.", "Chem. Rev", or primary literature sources identified by standard literature searches online or from secondary sources such as "Chemical Abstracts" or "Beilstein". Such literature methods include those of the preparative Examples herein, and methods analogous thereto.

Scheme 1 represents a method known in the art of organic chemistry in general, by which the compounds of the present invention may be prepared:

Scheme 1

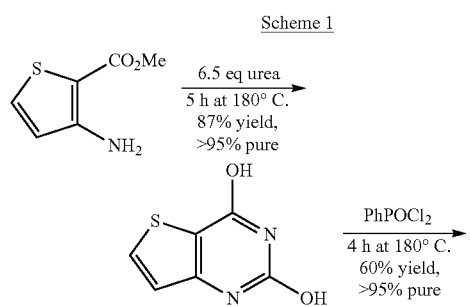

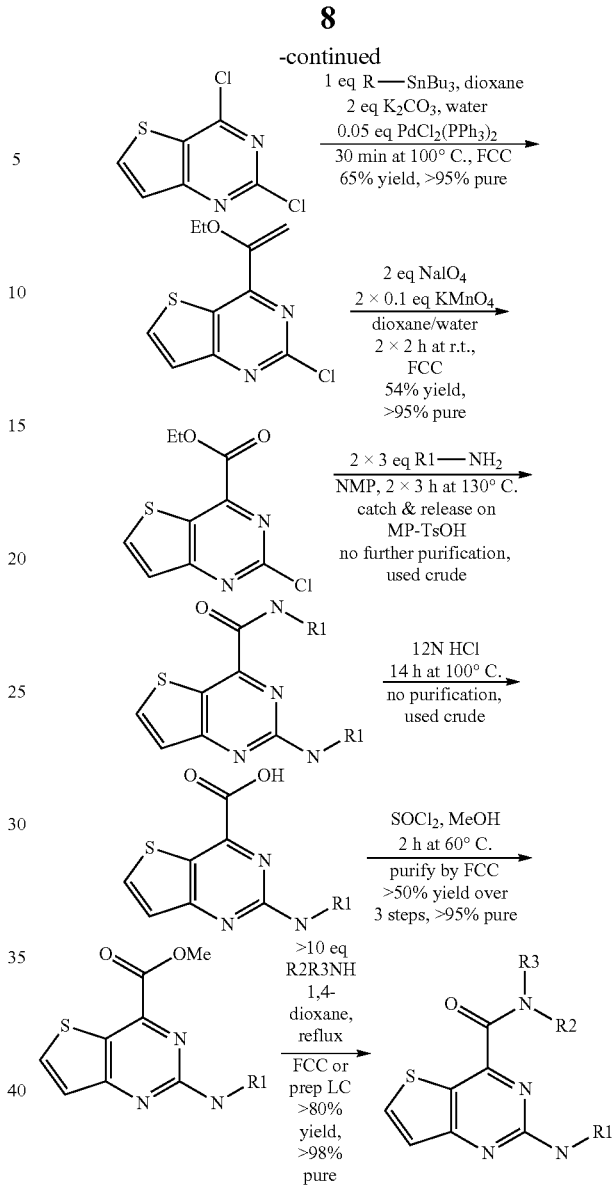

EXAMPLES

The following examples illustrate the preparation of specific compounds of the invention and are not intended to be limiting of the full scope of the invention.

Examples 1 to 6 relate to the method indicated in Scheme 1.

Preparative Example 1

Urea Cyclisation

Thieno[3,2-d]pyrimidine-2,4-diol

A solid mixture of methyl 3-aminothiophene-2-carboxylate (40.0 g, 254 mmol) and urea (99.4 g, 163 mmol) was stirred and heated to 180° C. for 5 h. The now semi-fluid mixture was cooled to 75-80° C. before water (800 ml) was added. After stirring at room temperature for 2 h the formed precipitate was filtered off, washed with further water and dried at 40° C. i. vac. Thieno[3,2-d]pyrimidine-2,4-diol was obtained as cream-coloured powder (37.15 g, 87% yield) of >95% purity.

LC-MS: m/z=169 [M+H$^+$]; RT=1.29 (LC-MS method 2)
$^1$H-NMR: $\delta_H$ (400 MHz, d$_6$-DMSO) 6.91 (1H, d, J 5.02 Hz), 8.04 (1H, d, J 5.02 Hz), 11.30 (2H, br s)

Preparative Example 2

Hydroxy-Chloro Exchange 2,4-Dichloro-thieno[3,2-d]pyrimidine

A mixture of Example 1 (20 g, 119 mmol) in phenylphosphonic dichloride (120 ml, 850 mmol) was stirred and heated to 180° C. for 4 h. The resulting dark solution was cooled to 80° C. and transferred slowly by pipette onto stirred ice/water (800 ml). After an hour of vigorous stirring, the yellow-orange precipitate was filtered off, washed and dried at 40° C. i. vac. The solid was dissolved in DCM (ca. 20 volumes). The solution was passed through a pad of silica and washed through with ethyl acetate:iso-hexane (1:1). The filtrate was reduced i. vac. to yield 2,4-dichloro-thieno[3,2-d]pyrimidine (14.56 g, 60% yield) as a yellow crystalline product.

LC-MS: m/z=205 [M+H$^+$]; RT=4.36 (LC-MS method 2)
$^1$H-NMR: $\delta_H$ (400 MHz, d$_6$-DMSO) 7.74 (1H, d, J 5.52 Hz), 8.70 (1H, d, J 5.52 Hz)

Preparative Example 3

Stille Coupling

2-Chloro-4-(1'-ethoxy-vinyl)-thieno[3,2-d]pyrimidine

To a solution of Example 2 (3.0 g, 14.6 mmol) in 1,4-dioxane (200 mL) was added a solution of K$_2$CO$_3$ (4.0 g, 29.3 mmol) in water (40 mL). The almost clear solution was placed under nitrogen atmosphere and (1-Ethoxyvinyl)-tributylstannane (5.0 mL, 14.6 mmol) and PdCl$_2$(PPh$_3$)$_2$ (500 mg, 0.731 mmol). The mixture was heated to 100° C. and stirred at 100° C. for 30 min under nitrogen atmosphere. After cooling to room temp. the 1,4-dioxane was removed i. vac. The residue was re-dissolved in DCM (100 mL) and water (50 mL) and transferred to a separating funnel. The aqueous layer was extracted with DCM (30 mL), the combined organic layers were washed with water (50 mL) and sat. brine (30 mL), dried over Na$_2$SO$_4$ and evaporated to dryness i. vac. The residue was purified by flash column chromatography (50 g SiO$_2$ Isolute® pre-wetted with 1CV DCM) eluting with neat DCM collecting 12 mL fractions. Desired product eluted in fractions 10 to 20 with R$_f$=0.31 (DCM). By-products eluted in fractions 6 to 9 (R$_f$=0.59 in DCM) and fractions 21-31 ((R$_f$=0.14 in DCM). Fractions 10 to 20 were combined and evaporated to dryness i. vac. providing 2.28 g (65% yield) 2-chloro-4-(1'-ethoxy-vinyl)-thieno[3,2-d]pyrimidine as yellow powder of 95% purity.

LC-MS: m/z=241 [M+H$^+$]; RT 3.38 (LC-MS method 1)
$^1$H-NMR: $\delta_H$ (400 MHz, d$_6$-DMSO) 1.49 (3H, t, J 7.03 Hz), 4.11 (2H, q, J 7.03 Hz), 4.88 (1H, d, J 2.51 Hz), 5.76 (1H, d, J 2.51 Hz), 7.59 (1H, d, J 5.52 Hz), 8.62 (1H, d, J 6.02 Hz)

Preparative Example 4

Ethyl 2-chloro-thieno[3,2-d]pyrimidine-4-carboxylate

NaIO$_4$ (1.07 g, 4.99 mmol) was suspended in water (13 mL) and sonicated until a clear solution (pH ~4) was obtained. This solution was added to a solution of Example 3 (600 mg, 2.49, mmol) in 1,4-dioxane (40 mL). KMnO$_4$ (40 mg, 0.249 mmol) was added and the reaction mixture was stirred at room temp for 2 h. Progress of the reaction was checked by TLC (DCM). If remaining starting material was detected, further KMnO$_4$ (40 mg, 0.249 mmol) was added and the reaction mixture was stirred at room temp for further 2 h. The mixture was adjusted to pH 7-8 with sat. aqueous K$_2$CO$_3$ solution (1-2 mL). The precipitate was filtered off and the residue was rinsed thoroughly with DCM (4×20 mL). The combined filtrates were washed with water, dried over Na$_2$SO$_4$ and evaporated to dryness i. vac. The residue was purified by flash column chromatography (10 g SiO$_2$ Isolute®, pre-wetted with 1CV DCM) eluting with neat DCM collecting 10 mL fractions. Ethyl 2-chloro-thieno[3,2-d]pyrimidine-4-carboxylate (325 mg, 54% yield) was isolated as colourless powder of 95% purity.

LC-MS: m/z=243 [M+H$^+$]; RT=2.92 (LC-MS method 1)
$^1$H-NMR: $\delta_H$ (400 MHz, d$_6$-DMSO) 1.41 (3H, t, J 7.03), 4.50 (2H, q, J 7.03 Hz), 7.72 (1H, d, J 5.52 Hz), 8.76 (1H, d, J 6.02 Hz)

General Procedure 1

To a solution of Example 4 (200 mg, 0.824 mmol) in NMP (4 mL) was added R1 amine (2.47 mmol). The reaction mixture was shaken at 130° C. for 3 h. Further R1 amine (2.47 mmol) was added and shaking at 130° C. was continued for further 3 h. After cooling to room temperature the mixture was transferred to a separating funnel with DCM (20 mL) and washed with water (3×10 mL). The organic layer was loaded onto MP-TsOH (1 g, Argonaut, pre-wetted with neat DCM). The resin was rinsed with DCM (30 mL) and 2-amino substituted thieno[3,2-d]pyrimidine-4-carboxamide eluted with 0.2 N NH$_3$ in DCM/MeOH (prepared from 2 mL 7N NH$_3$ in MeOH+60 mL DCM+8 mL MeOH) as intensively yellow fractions. Fractions were combined and evaporated to dryness i. vac.

The crude intermediate was dissolved in 12N aq HCl (10 mL) and evaporated to dryness i. vac. at a bath temperature of 80° C. The residue was re-dissolved in 12N aq HCl (12 mL) and stirred at 100° C. for 14 h. The reaction mixture was evaporated to dryness i. vac. at a bath temperature of 80° C., re-dissolved in MEOH and evaporated to dryness again to obtain 2-amino substituted thieno[3,2-d]pyrimidine-4-carboxylic acid as a yellow-brownish solid.

The crude acid was dissolved in MEOH (20 mL) and thionylchloride (360 µL, 4.94 mmol) was added dropwise at room temp. The mixture was stirred at 60° C. for 2.5 h and then evaporated to dryness i. vac. The residue was dissolved in DCM/MEOH (10:1, 100 mL), washed with sat aqueous NaHCO$_3$ (50 mL) and sat. brine (50 mL), dried over Na$_2$SO$_4$ and evaporated to dryness i. vac. The residue was purified by column chromatography (10 g SiO$_2$ Isolute® pre-wetted with 1CV DCM/MEOH 50:1) eluting with DCM/MEOH 50:1 collecting 5 mL fractions. Fractions were combined and evaporated to dryness i. vac. providing >50% yield of 2-amino substituted thieno[3,2-d]pyrimidine-4-methyl ester as a yellow solid of >95% purity.

The following analogues were prepared using general procedure 1.

Preparative Example 5

2-[(Pyridin-3-ylmethyl)-amino]thieno[3,2-d]pyrimidine-4-carboxylic acid methyl ester LC-MS: m/z=301 [M+H$^+$]; RT=2.44 (LC-MS method 1)
$^1$H-NMR: $\delta_H$ (400 MHz, d$_6$-DMSO) 3.97 (3H, s), 4.60 (2H, d, J 6.02 Hz), 7.28 (1H, d, J 5.52 Hz), 7.31 (1H, m), 7.77 (1H, m), 8.14 (1H, br s), 8.34 (1H, d, J 5.52 Hz), 8.42 (1H, m), 8.60 (1H, br s)

Preparative Example 6

2-(1-Pyridin-3-yl-ethylamino)-thieno[3,2-d]pyrimidine-4-carboxylic acid methyl ester LC-MS: m/z=315 [M+H$^+$]; RT=2.47 (LC-MS method 1)
$^1$H-NMR: $\delta_H$ (400 MHz, d$_6$-DMSO) 1.51 (3H, d, J 7.03 Hz), 3.96 (3H, s), 5.21 (1H, m), 7.24 (1H, d, J 5.52 Hz), 7.31 (1H, m), 7.83 (1H, dt, J 7.53, 2.01 Hz), 8.19 (1H, br s), 8.31 (1H, d, J 5.52 Hz), 8.39 (1H, dd, J 5.02, 1.51 Hz), 8.66 (1H, d, J 2.01 Hz)

General Procedure 2

To a solution of the corresponding example 5 or 6 (0.50 mmol) in 1,4-dioxane (4 mL) was added the required amine (>10 eq). The mixture was stirred under reflux for 1 h. After cooling to room temp the mixture was evaporated to dryness i. vac. and the residue was purified by flash column chromatography (5 g SiO$_2$ Isolute® pre-wetted with EtOAc). Crude material was loaded as a solution in a minimum neat DCM and product was eluted with neat EtOAc collecting 6 mL fractions. Fractions were combined and evaporated to dryness i. vac. providing >80% yield 2-amino substituted thieno[3,2-d]pyrimidin-4-carboxamide as yellow powder of >95% purity.

The following analogues were prepared using general procedure 2.

Example 7

[2-(1-Pyridin-3-yl-ethylamino)-thieno[3,2-d]pyrimidin-4-yl]-pyrrolidin-1-yl-methanone

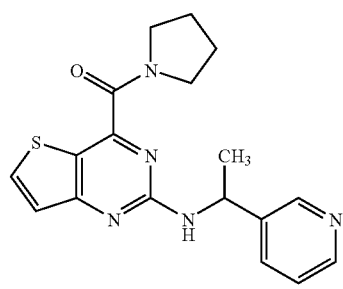

LC-MS: m/z=345 [M+H$^+$]; RT=2.52 (LC-MS method 1)
$^1$H-NMR: $\delta_H$ (400 MHz, d$_6$-DMSO) 1.52 (3H, d, J 7.03 Hz), 1.81 (4H, m), 3.52 (2H, m), 3.82 (2H, m), 5.17 (1H, m), 7.19 (1H, d, J 5.52 Hz), 7.31 (1H, m), 7.80 (1H, dt, J 8.03, 2.01 Hz), 7.84 (1H, d, J 7.53 Hz), 8.24 (1H, d, J 5.52 Hz), 8.40 (1H, dd, J 5.02, 1.51 Hz), 8.63 (1H, d, J 2.51 Hz)

Example 8

2-[(Pyridin-3-ylmethyl)-amino]-thieno[3,2-d]pyrimidine-4-carboxylic acid ethylamide

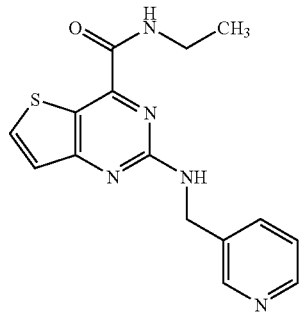 [SMILES: CCNC(=O)c1nc(NCc2cccnc2)nc2ccsc12]

LC-MS: m/z=314 [M+H$^+$]; RT=1.59 (LC-MS method 1)
$^1$H-NMR: $\delta_H$ (400 MHz, d$_6$-DMSO) 1.15 (3H, t, J 7.07 Hz), 3.38 (2H, q, J 7.07 Hz), 4.70 (2H, br s), 7.22 (1H, d, J 5.56 Hz), 7.34 (1H, dd, J 7.83, 4.80 Hz), 7.80 (2H, m), 8.32 (1H, d, J 5.56 Hz), 8.43 (1H, d, J 4.55 Hz), 8.64 (1H, s), 8.81 (1H, br s)

Example 9

{2-[(Pyridin-3-ylmethyl)-amino]-thieno[3,2-d]pyrimidin-4-yl}-pyrrolidin-1-yl-methanone

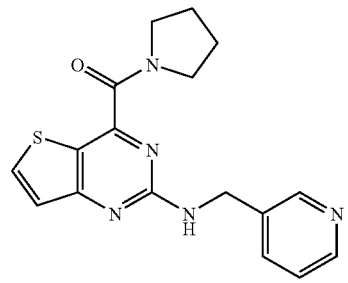 [SMILES: O=C(c1nc(NCc2cccnc2)nc2ccsc12)N1CCCC1]

LC-MS: m/z=340 [M+H$^+$]; RT=2.42 (LC-MS method 1)
$^1$H-NMR: $\delta_H$ (400 MHz, d$_6$-DMSO) 1.81 (4H, m), 3.54 (2H, t, J 6.53 Hz), 3.78 (2H, br s), 4.60 (2H, d, J 6.02 Hz), 7.23 (1H, d, J 5.52 Hz), 7.32 (1H, m), 7.74 (1H, d, J 7.53 Hz), 7.88 (1H, t, J 6.02 Hz), 8.27 (1H, d, J 6.02 Hz), 8.43 (1H, dd, J 4.52, 1.51 Hz), 8.57 (1H, s)

Example 10

2-[(Pyridin-3-ylmethyl)-amino]-thieno[3,2-d]pyrimidine-4-carboxylic acid cyclopropylamide

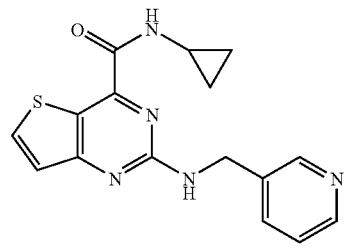 [SMILES: O=C(NC1CC1)c1nc(NCc2cccnc2)nc2ccsc12]

LC-MS: m/z=326 [M+H⁺]; RT=2.39 (LC-MS method 1)

¹H-NMR: δ$_H$ (400 MHz, d$_6$-DMSO) 0.68 (2H, m), 0.77 (2H, m), 2.90 (1H, m), 4.67 (2H, d, J 6.02 Hz), 7.22 (1H, d, J 5.52 Hz), 7.31 (1H, m), 7.76 (2H, m), 8.32 (1H, d, J 5.52 Hz), 8.42 (1H, br d, J 4.52 Hz), 8.61 (2H, m)

Example 11

2-[(Pyridin-3-ylmethyl)-amino]-thieno[3,2-d]pyrimidine-4-carboxylic acid isopropylamide

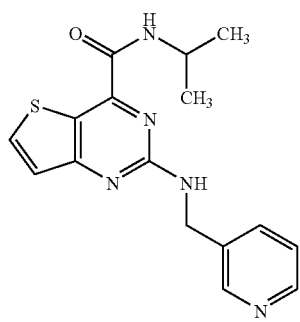 [SMILES: CC(C)NC(=O)c1nc(NCc2cccnc2)nc2ccsc12]

LC-MS: m/z=328 [M+H⁺]; RT=1.74 (LC-MS method 1)

¹H-NMR: δ$_H$ (400 MHz, d$_6$-DMSO) 1.22 (6H, d, J 6.57 Hz), 4.10 (1H, m), 4.65 (2H, br d, J 5.56 Hz), 7.23 (1H, d J 5.31 Hz), 7.34 (1H, m), 7.80 (1H, dm, J 7.83 Hz), 7.89 (1H, m), 8.32 (1H, d, J=8.34 Hz), 8.33 (1H, d, J 5.56 Hz), 8.43 (1H, dd, J 4.55, 1.26 Hz), 8.64 (1H, s)

Example 12

2-[(Pyridin-3-ylmethyl)-amino]thieno[3,2-d]pyrimidine-4-carboxylic acid cyclopentylamide

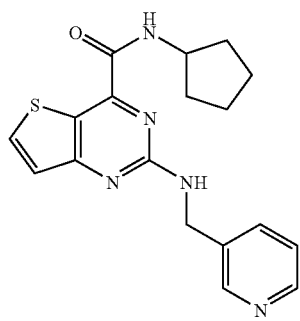 [SMILES: O=C(NC1CCCC1)c1nc(NCc2cccnc2)nc2ccsc12]

LC-MS: m/z=354 [M+H⁺]; RT=1.95 (LC-MS method 1)

¹H-NMR: δ$_H$ (400 MHz, d$_6$-DMSO) 1.58 (4H, m), 1.71 (2H, m), 1.93 (2H, m), 4.23 (1H, m), 4.64 (2H, d, J 5.56 Hz), 7.23 (1H, d, J 5.56 Hz), 7.32 (1H, dd, J 7.83, 4.80 Hz), 7.77 (1H, dt, J 7.83, 1.90 Hz), 7.89 (1H, br s), 8.33 (1H, d, J 5.56 Hz), 8.35 (1H, m), 8.42 (1H, dd, J 4.55, 1.52 Hz), 8.62 (1H, s)

Example 13

2-[(Pyridin-3-ylmethyl)-amino]-thieno[3,2-d]pyrimidine-4-carboxylic acid methylamide

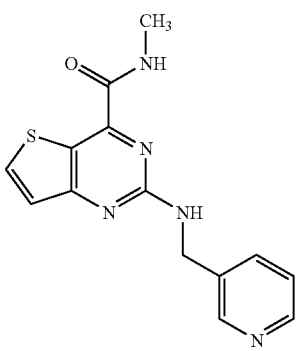 [SMILES: CNC(=O)c1nc(NCc2cccnc2)nc2ccsc12]

LC-MS: m/z=300 [M+H⁺]; RT=1.46 (LC-MS method 1)

¹H-NMR: δ$_H$ (400 MHz, d$_6$-DMSO) 2.88 (3H, d, J 5.05 Hz), 4.72 (2H, m), 7.21 (1H, d, J 5.56 Hz), 7.34 (1H, dd, J 7.83, 4.80 Hz), 7.79 (2H, dm, J 7.83 Hz), 832 (1H, d, J 5.56 Hz), 8.43 (1H, dd, J 4.55, 1.01 Hz), 8.63 (1H, s), 8.84 (1H, br s)

Example 14

2-[(Pyridin-3-ylmethyl)-amino]-thieno[3,2-d]pyrimidine-4-carboxylic acid phenethyl-amide

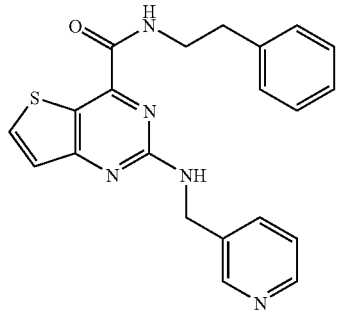 [SMILES: O=C(NCCc1ccccc1)c1nc(NCc2cccnc2)nc2ccsc12]

LC-MS: m/z=390 [M+H⁺]; RT=2.07 (LC-MS method 1)

¹H-NMR: δ$_H$ (400 MHz, d$_6$-DMSO) 2.88 (2H, t, J 7.33), 3.58 (2H, m), 4.69 (2H, m), 7.17-7.34 (7H, m), 7.75 (1H, dm,

J 7.83 Hz), 7.82 (1H, br s), 8.33 (1H, d, J 5.56 Hz), 8.43 (1H, dd, J 4.80, 1.26 Hz), 8.61 (1H, m), 8.85 (1H, br s)

Example 15

2-[(Pyridin-3-ylmethyl)-amino]-thieno[3,2-d]pyrimidine-4-carboxylic acid cyclohexylamide

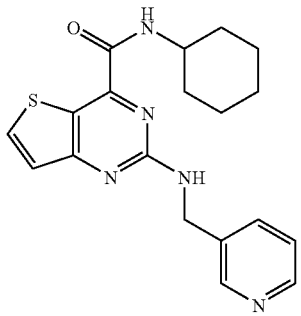 [SMILES: O=C(NC1CCCCC1)c1nc(NCc2cccnc2)nc2ccsc12]

LC-MS: m/z=368 [M+H$^+$]; RT=2.10 (LC-MS method 1)
$^1$H-NMR: $\delta_H$ (400 MHz, d$_6$-DMSO) 1.13-1.45 (5H, m), 1.60 (1H, m), 1.72 (2H, m), 1.82 (2H, m), 3.78 (1H, m), 4.64 (2H, m), 7.23 (1H, d, J 5.05 Hz), 7.32 (1H, m), 7.78 (1H, d, J 7.33 Hz), 7.90 (1H, br s), 8.32 (2H, m), 8.42 (1H, br d, J 4.04 Hz), 8.62 (1H, s)

Example 16

2-[(Pyridin-3-ylmethyl)-amino]-thieno[3,2-d]pyrimidine-4-carboxylic acid benzylamide

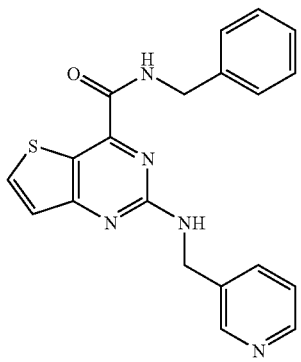 [SMILES: O=C(NCc1ccccc1)c1nc(NCc2cccnc2)nc2ccsc12]

LC-MS: m/z=376 [M+H$^+$]; RT=1.99 (LC-MS method 1)
$^1$H-NMR: $\delta_H$ (400 MHz, d$_6$-DMSO) 4.56 (2H, d, J 6.32 Hz), 4.71 (2H, br s), 7.21-7.31 (3H, m), 7.32-7.35 (4H, m), 7.78 (1H, dm, J 7.83 Hz), 7.84 (1H, br s), 8.33 (1H, d, J 5.56 Hz), 8.41 (1H, m), 8.63 (1H, s), 9.37 (1H, br s)

Example 17

2-[(Pyridin-3-ylmethyl)-amino]-thieno[3,2-d]pyrimidine-4-carboxylic acid (2-methoxy-ethyl)-amide

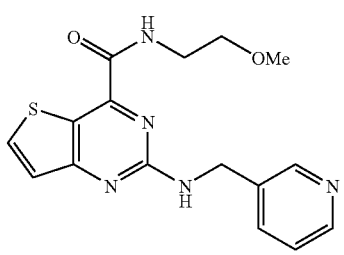 [SMILES: COCCNC(=O)c1nc(NCc2cccnc2)nc2ccsc12]

LC-MS: m/z=344 [M+H$^+$]; RT=2.35 (LC-MS method 1)
$^1$H-NMR: $\delta_H$ (400 MHz, d$_6$-DMSO) 3.30 (2H, m, under DMSO.H$_2$O), 3.51 (5H, m), 4.67 (2H, br d, J 6.02 Hz), 7.23 (1H, d, J 5.52 Hz), 7.32 (1H, m), 7.78 (1H, dt, J 7.53, 2.01 Hz), 7.85 (1H, t, J 6.53 Hz), 8.33 (1H, d, J 5.52 Hz), 8.42 (1H, dd, J 5.02, 1.51 Hz), 8.63 (2H, br m)

Example 18

2-[(Pyridin-3-ylmethyl)-amino]-thieno[3,2-d]pyrimidine-4-carboxylic acid (pyridin-3-ylmethyl)-amide

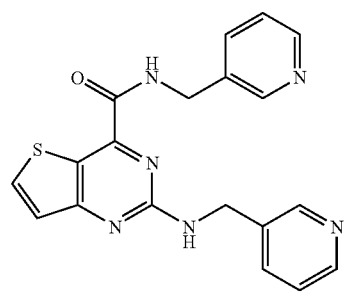 [SMILES: O=C(NCc1cccnc1)c1nc(NCc2cccnc2)nc2ccsc12]

LC-MS: m/z=377 [M+H$^+$]; RT=2.46 (LC-MS method 1)
$^1$H-NMR: $\delta_H$ (400 MHz, d$_6$-DMSO) 4.58 (2H, d, J 6.02 Hz), 4.71 (2H, d, J 5.52 Hz), 7.22 (1H, d J 5.52 Hz), 7.29 (1H, m), 7.37 (1H, m), 7.76 (3H, m), 8.33 (1H, d, J 5.52 Hz), 8.42 (1H, dd, J 5.02, 1.51 Hz), 8.48 (1H, dd, J 5.02, 1.51 Hz), 8.58 (1H, m), 8.63 (1H, m), 9.41 (1H, br s)

Example 19

Piperidin-1-yl-{2-[(pyridin-3-ylmethyl)-amino]-thieno[3,2-d]pyrimidin-4-yl}-methanone

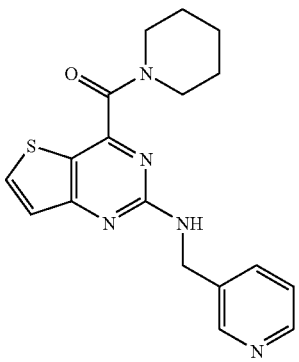 [SMILES: O=C(c1nc(NCc2cccnc2)nc2ccsc12)N1CCCCC1]

LC-MS: m/z=354 [M+H$^+$]; RT=1.66 (LC-MS method 1)
$^1$H-NMR: $\delta_H$ (400 MHz, d$_6$-DMSO) 1.31-1.48 (2H, m), 1.58 (4H, m), 3.41 (2H, m), 3.61 (2H, m), 4.57 (2H, d, J 6.06 Hz), 7.25 (1H, d, J 5.56 Hz), 7.32 (1H, m), 7.73 (1H, br d, J 7.33 Hz), 7.96 (1H, m), 8.28 (1H, d, J 5.56 Hz), 8.42 (1H, m), 8.56 (1H, s)

Crude 2-amino substituted thieno[3,2-d]pyrimidine-4-methyl ester, before purification by column chromatography, could also be used as starting material for the amide formation, however, this left a more difficult final purification. Using this procedure the following product was isolated together with the 2-$NH_2$ analogue as by-product.

Example 20

2-(1-Pyridin-3-yl-ethylamino)-thieno[3,2-d]pyrimidine-4-carboxylic acid cyclopropylamide

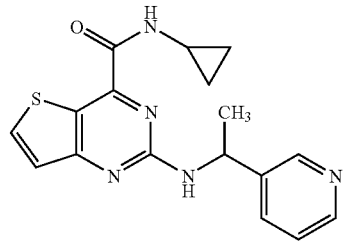 [SMILES: CC(Nc1nc(C(=O)NC2CC2)c2sccc2n1)c1cccnc1]

LC-MS: m/z=340 [M+$H^+$]; RT=2.46 (LC-MS method 1)
$^1$H-NMR: $\delta_H$ (400 MHz, $d_6$-DMSO) 0.67 (2H, m), 0.78 (2H, m), 1.51 (3H, d, J 7.03 Hz), 2.90 (1H, m), 5.33 (1H, br m), 7.19 (1H, d, J 5.52 Hz), 7.31 (1H, m), 7.78 (1H, br m), 7.84 (1H, dt, J 8.03, 2.01 Hz), 8.30 (1H, d, J 5.52 Hz), 8.39 (1H, dd, J 4.52, 1.51 Hz), 8.49 (1H, br d, J 4.52 Hz), 8.69 (1H, br d, J 2.01 Hz)

Example 21

2-Amino-thieno[3,2-d]pyrimidine-4-carboxylic acid cyclopropylamide

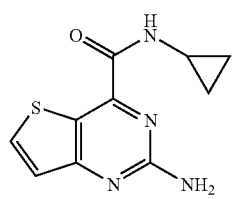

LC-MS: m/z=235 [M+$H^+$]; RT=2.34 (LC-MS method 1)
$^1$H-NMR: $\delta_H$ (400 MHz, $d_6$-DMSO) 0.69 (2H, m), 0.76 (2H, m), 2.91 (1H, m), 6.61 (2H, s), 7.19 (1H, d, J 5.52 Hz), 8.31 (1H, d, J 5.52 Hz), 8.59 (1H, d, J 4.52 Hz)

Example 22

(R-[2-(1-Pyridin-3-yl-ethylamino)-thieno[3,2-d]pyrimidin-4-yl]pyrrolidin-1-yl-methanone

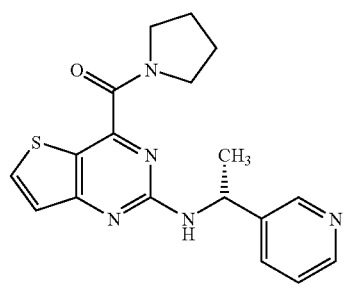

Prepared as per example 7, using (R)-1-Pyridin-3-yl-ethylamine, which was itself obtained via the resolution protocol described in Smith et. al., Journal of the American Chemical Society, 1973, 95, pp 811-818. Example 22 had spectroscopic properties identical to the racemic example 7. Chiral LC RT=45.40 min Example 23

(S)-[2-(1-Pyridin-3-yl-ethylamino)-thieno[3,2-d]pyrimidin-4-yl]-pyrrolidin-1-yl-methanone

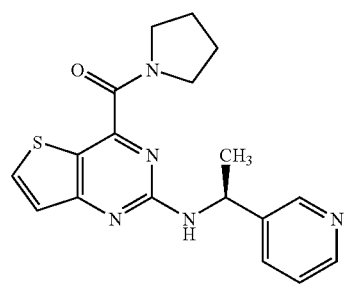 [SMILES: C[C@H](Nc1nc(C(=O)N2CCCC2)c2sccc2n1)c1cccnc1]

Prepared as per example 7, using (S)-1-Pyridin-3-yl-ethylamine, which was itself obtained via the resolution protocol described in Smith et. al., Journal of the American Chemical Society, 1973, 95, pp 811-818. Example 23 had spectroscopic properties identical to the racemic example 7. Chiral LC RT=30.40 min General Procedures All reagents obtained from commercial sources were used without further purification. Anhydrous solvents were obtained from commercial sources and used without further drying. Flash chromatography was performed with pre-packed silica-gel cartridges (Strata Si-1, 61 Å, Phenomenex, Cheshire, UK or IST Flash II, 54 Å, Argonaut, Hengoed, UK). Thin layer chromatography was conducted with 5×10 cm plates coated with Merck Type 60 $F_{254}$ silica-gel. Microwave heating was performed with a Biotage Initiator™ 2.0 instrument.

The compounds of the present invention were characterized by liquid chromatography-mass spectroscopy (LC-MS) using the following methods.

LC-MS Method 1

Instrument: Waters 2695 pump and 2700 sample manager Waters ZQ2000, M/z range 100 to 900 amu Column: Gemini 5 µm, C18 110A, 30 mm×2 mm from Phenomenex. Pt no 00A-4435-B0

Temperature: Ambient

Mobile Phase:
  A–Water+10 mMol/ammonium formate+0.04% (v/v) formic acid at pH ca 3.5
  B–100% Acetonitrile+0.04% (v/v) formic acid Injection Volume 10 uL Gradient:

| Time (min) | Solvent A (%) | Solvent B (%) | Flow (cm³min⁻¹) |
|---|---|---|---|
| −0.8 (Equil) | 95 | 5 | 1.0 |
| 0 | 95 | 5 | 0.8 |
| 0.25 | 95 | 5 | 0.8 |
| 2.50 | 5 | 95 | 0.8 |
| 4.0 | 5 | 95 | 0.8 |
| 5 | 5 | 95 | 1.0 |
| 5.2 | 95 | 5 | 1.0 |

Detection: UV detection from 220 to 400 nm (1:3 split MS to UV)
LC-MS Method 2
Instrument: Waters 2695 pump and 2700 sample manager Waters ZQ2000, M/z range 100 to 900 amu
Column: Gemini 5 μm, C18 110A, 30 mm×2 mm from Phenomenex. Pt no 00A-4435-B0
Temperature: Ambient
Mobile Phase:
  A−Water+10 mMol/ammonium formate+0.04% (v/v) formic acid at pH ca 3.5
  B−100% Acetonitrile+0.04% (v/v) formic acid
Injection Volume 5 uL
Gradient:

| Time (min) | Solvent A (%) | Solvent B (%) | Flow (cm³min⁻¹) |
|---|---|---|---|
| 0 | 95 | 5 | 0.4 |
| 0.5 | 95 | 5 | 0.4 |
| 3 | 5 | 95 | 0.4 |
| 6 | 5 | 95 | 0.4 |
| 6.5 | 95 | 5 | 0.4 |

Detection: UV detection from 220 to 400 nm

Nuclear magnetic resonance (NMR) analysis was performed with a Bruker DPX400 spectrometer and proton NMR spectra were measured at 400 MHz. The spectral reference was the known chemical shift of the solvent. Proton NMR data is reported as follows: chemical shift (δ) in ppm, followed by the integration, the multiplicity (where s=singlet, d=doublet, t=triplet, q=quartet, p=pentet, m=multiplet, dd=doublet of doublets and br=broad), and the coupling constant rounded to the nearest 0.1 Hz.

Some compounds of the invention were purified by preparative HPLC. These were performed on a Waters Fraction-Lynx MS autopurification system, with a Gemini® 5 μm C18(2), 100 mm×20 mm i.d. column from Phenomenex, running at a flow rate of 20 cm³min⁻¹ with UV diode array detection (210-400 nm) and mass-directed collection. Gradients used for each compound are shown in Table 1.

At pH 4: solvent A=10 mM ammonium acetate in HPLC grade water+0.08% v/v formic acid. Solvent B=95% v/v HPLC grade acetonitrile+5% v/v solvent A+0.08% v/v formic acid.

At pH 9: solvent A=10 mM ammonium acetate in HPLC grade water+0.08% v/v ammonia solution. Solvent B=95% v/v HPLC grade acetonitrile+5% v/v solvent A+0.08% v/v ammonia solution.

The mass spectrometer was a Waters Micromass ZQ2000 spectrometer, operating in positive or negative ion electrospray ionisation modes, with a molecular weight scan range of 150 to 1000.

TABLE 1

Preparative HPLC gradients

| Time (min) | % Solvent B for Example No. | | | | | |
|---|---|---|---|---|---|---|
| | 4, 5 and 14 | 6, 8, 11, 12, 15-18, 21 and 26 | 19, 20 and 23 | 2, 3, 9, 10 and 13 | 24 | 27 |
| 0.0 | 5 | 5 | 5 | 5 | 5 | 5 |
| 0.5 | 6 | 15 | 15 | 30 | 10 | 25 |
| 7.0 | 25 | 30 | 40 | 40 | 20 | 50 |
| 7.5 | 95 | 95 | 95 | 95 | 95 | 95 |
| 9.5 | 95 | 95 | 95 | 95 | 95 | 95 |
| 10 | 5 | 5 | 5 | 5 | 5 | 5 |

Those compounds of the invention were analyded by chiral HPLC using the method detailed below.

Instrument: Perkin Elmer Series 250 HPLC, equipped with a Perkin Elmer 785A UV/Visible detector Column: ChiralPak AD-H column, 250×4.6 mm Temperature: 30° C.

Mobile Phase: 80% isohexane, 20% iso-propyl alcohol, 0.1% Diethylamine, 1 mL/min, 60 min run time Detection: UV detection at 265 nM Injection Volume 10 μL IUPAC chemical names were generated using AutoNom Standard.

Assay Description

The use of a Fluorometric Imaging Plate Reader (FLIPR) to measure calcium flux in Adenosine-receptor expressing cells is a well-established technique. In this assay calcium flux is triggered by receptor activation and measured through the fluorescence of an incorporated calcium-sensitive dye. The potencies shown were determined using expressed human adenosine $A_{2B}$ receptors in mammalian cell lines. Selectivity values were obtained by using mammalian cell lines expressing the human adenosine $A_1$, $A_{2A}$, and $A_3$ receptors. Compound potency was determined from dose response curves and are reported as $IC_{50}$ values.

The compounds tested in the above assay were assigned to one of two activity ranges, namely A=$IC_{50}$<500 nM, or B=$IC_{50}$>500 nM, as indicated in Table 2 below.

TABLE 2

| Example | Activity |
|---|---|
| 7 | B |
| 8 | B |
| 9 | A |
| 10 | B |
| 11 | A |
| 12 | B |
| 13 | B |
| 14 | A |
| 15 | A |
| 16 | A |
| 17 | B |
| 18 | B |
| 19 | B |
| 20 | A |
| 21 | B |
| 22 | B |
| 23 | A |

The invention claimed is:

1. A compound of formula (I) or a pharmaceutically acceptable salt, thereof:

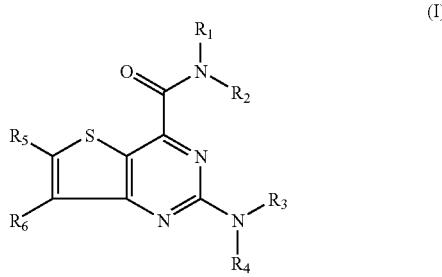

wherein
- $R_1$ and $R_2$ are independently selected from hydrogen, or optionally substituted $C_1$-$C_6$ alkyl, $C_1$-$C_6$ alkoxy-($C_1$-$C_6$)-alkyl, $C_3$-$C_8$ cycloalkyl, aryl, heteroaryl, aryl-($C_1$-$C_6$)-alkyl, or heteroaryl-($C_1$-$C_6$)-alkyl;
- or $R_1$ and $R_2$ taken together with the nitrogen atom to which they are attached form an optionally substituted 5- or 6-membered ring;
- $R_3$ and $R_4$ are independently selected from hydrogen, or optionally substituted $C_1$-$C_6$ alkyl, $C_1$-$C_6$ alkoxy-($C_1$-$C_6$)-alkyl, $C_3$-$C_8$ cycloalkyl, aryl, heteroaryl, aryl-($C_1$-$C_6$)-alkyl, or heteroaryl-($C_1$-$C_6$)-alkyl;
- or $R_3$ and $R_4$ taken together with the nitrogen atom to which they are attached form an optionally substituted 5- or 6-membered ring;
- $R_5$ and $R_6$ are independently selected from hydrogen, $C_1$-$C_6$ alkyl, aryl, aryl-($C_1$-$C_6$)-alkyl, —$NHR_7$, —N(—$R_8$)—$R_9$, —NH—(C=O)—$R_{10}$, —(C=O)—NH—$R_{11}$, —(C=O)—O—$R_{12}$, or halo; and
- $R_7$, $R_8$, $R_9$, $R_{10}$, $R_{11}$, and $R_{12}$ are independently selected from $C_1$-$C_6$ alkyl, aryl, aryl-($C_1$-$C_6$)-alkyl and heteroaryl.

2. A compound as claimed in claim 1 wherein $R_1$ is hydrogen, $C_1$-$C_6$ alkyl, $C_1$-$C_6$ alkoxy-($C_1$-$C_6$)-alkyl, $C_3$-$C_8$ cycloalkyl, aryl-($C_1$-$C_6$)-alkyl, or heteroaryl-($C_1$-$C_6$)-alkyl.

3. A compound as claimed in claim 1 wherein $R_1$ is hydrogen, methyl, ethyl, isopropyl, 2-methoxy-ethyl, cyclopropyl, cyclopentyl, cyclohexyl, benzyl, 2-phenyl-ethyl, or pyrid-3-yl-methyl.

4. A compound as claimed in claim 1 wherein $R_1$ is methyl or ethyl.

5. A compound as claimed in claim 1 wherein $R_2$ is hydrogen, $C_1$-$C_6$ alkyl, $C_1$-$C_6$ alkoxy-($C_1$-$C_6$)-alkyl, $C_3$-$C_8$ cycloalkyl, aryl-($C_1$-$C_6$)-alkyl, or heteroaryl-($C_1$-$C_6$)-alkyl.

6. A compound as claimed in claim 5 wherein $R_2$ is hydrogen, methyl, ethyl, isopropyl, 2-methoxy-ethyl, cyclopropyl, cyclopentyl, cyclohexyl, benzyl, 2-phenyl-ethyl, or pyrid-3-yl-methyl.

7. A compound as claimed in claim 5 wherein $R_2$ is methyl or ethyl.

8. A compound as claimed in claim 1 wherein $R_1$ and $R_2$ taken together with the nitrogen atom to which they are attached form an optionally substituted 5- or 6-membered ring.

9. A compound as claimed in claim 8 wherein $R_1$ and $R_2$ taken together with the nitrogen atom to which they are attached form a pyrrolidine or piperidine ring optionally substituted by fluoro, chloro, bromo, cyano, methyl, trifluoromethyl, ethyl, hydroxyl, hydroxymethyl, or hydroxyethyl.

10. A compound as claimed in claim 8 wherein $R_1$ and $R_2$ taken together with the nitrogen atom to which they are attached form pyrrolidin-1-yl or piperidin-1-yl.

11. A compound as claimed in claim 1 wherein $R_3$ is hydrogen or heteroaryl-($C_1$-$C_6$)-alkyl.

12. A compound as claimed in claim 1 wherein $R_4$ is hydrogen or heteroaryl-($C_1$-$C_6$)-alkyl.

13. A compound as claimed in claim 1 wherein $R_3$ is hydrogen and $R_4$ is heteroaryl-($C_1$-$C_6$)-alkyl.

14. A compound as claimed in claim 1 wherein $R_5$ is hydrogen.

15. A compound as claimed in claim 1 wherein $R_6$ is hydrogen.

16. A compound of formula (II) or a pharmaceutically acceptable salt, thereof:

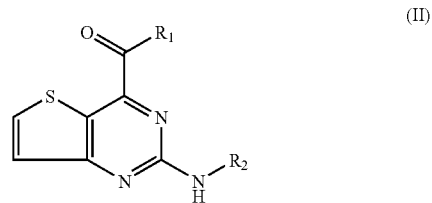

wherein
- $R_1$ is —NH—$R_3$ or an optionally substituted monocyclic 5- or 6-membered nitrogen-containing ring coupled via a nitrogen atom;
- $R_2$ is $C_1$-$C_6$ alkyl substituted by an optionally substituted 5- or 6-membered heteroaryl ring; and
- $R_3$ is hydrogen, $C_1$-$C_6$ alkyl, $C_1$-$C_6$ alkoxy-($C_1$-$C_6$)-alkyl, $C_3$-$C_8$ cycloalkyl, aryl-($C_1$-$C_6$)-alkyl, or heteroaryl-($C_1$-$C_6$)-alkyl.

17. A compound as claimed in claim 16 wherein $R_1$ is an optionally substituted monocyclic 5- or 6-membered nitrogen-containing ring coupled via a nitrogen atom.

18. A compound as claimed in claim 16 wherein $R_1$ is a pyrrolidine or piperidine ring optionally substituted by fluoro, chloro, bromo, cyano, methyl, trifluoromethyl, ethyl, hydroxyl, hydroxymethyl, or hydroxyethyl.

19. A compound as claimed in claim 16 wherein $R_1$ is pyrrolidin-1-yl or piperidin-1-yl.

20. A compound as claimed in claim 16 wherein $R_1$ is $C_1$-$C_6$ alkylamino or $C_3$-$C_8$ cycloalkylamino.

21. A compound as claimed in claim 20 wherein $R_1$ is methylamino, ethylamino, isopropylamino, or cyclopropylamino.

22. A compound as claimed in claim 16 wherein $R_2$ is methyl- or ethyl-substituted by an optionally substituted 5- or 6-membered heteroaryl ring.

23. A compound as claimed in claim 16 wherein $R_2$ is methyl- or ethyl-substituted by a 5- or 6-membered heteroaryl ring optionally substituted by fluoro, chloro, bromo, cyano, methyl, trifluoromethyl, ethyl, hydroxyl, hydroxymethyl, or hydroxyethyl.

24. A compound as claimed in claim 16 wherein $R_2$ is $C_1$-$C_6$ alkyl substituted by pyridyl.

25. A compound as claimed in claim 16 wherein $R_2$ is pyrid-3-ylmethyl or 1-(pyrid-3-yl)ethyl.

26. A pharmaceutical composition comprising a compound as claimed in claim 1 and a pharmaceutically acceptable carrier.

* * * * *

UNITED STATES PATENT AND TRADEMARK OFFICE
CERTIFICATE OF CORRECTION

PATENT NO. : 8,354,415 B2  Page 1 of 1
APPLICATION NO. : 12/678376
DATED : January 15, 2013
INVENTOR(S) : Jordan et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 402 days.

Signed and Sealed this
First Day of September, 2015

Michelle K. Lee
*Director of the United States Patent and Trademark Office*